United States Patent [19]

Cook et al.

[11] Patent Number: 4,807,476
[45] Date of Patent: Feb. 28, 1989

[54] VARIABLE ANGLE TRANSDUCER SYSTEM AND APPARATUS FOR PULSE ECHO INSPECTION OF LAMINATED PARTS THROUGH A FULL RADIAL ARC

[75] Inventors: James E. Cook, Seattle; James C. Kennedy; Fred D. Young, both of Bellevue, Wash.

[73] Assignee: The Boeing Company, Seattle, Wash.

[21] Appl. No.: 945,108

[22] Filed: Dec. 22, 1986

[51] Int. Cl.⁴ ............................................. G01N 29/00
[52] U.S. Cl. ...................................... 73/620; 73/629; 73/633
[58] Field of Search ................ 73/618, 620, 623, 633, 73/632, 629, 642; 310/336; 367/151

[56] References Cited

U.S. PATENT DOCUMENTS

| | | | |
|---|---|---|---|
| 3,163,784 | 12/1964 | Renaut | 310/336 |
| 4,361,044 | 11/1982 | Kupperman et al. | 73/623 |
| 4,466,286 | 8/1984 | Berbee et al. | 73/633 |
| 4,508,122 | 4/1985 | Gardineer et al. | 73/620 |

Primary Examiner—Stewart J. Levy
Assistant Examiner—Lawrence G. Fess
Attorney, Agent, or Firm—Conrad O. Gardner; B. A. Donahue

[57] ABSTRACT

A system and apparatus for ultrasonic pulse echo inspection of corners in laminated parts. A variable angle transducer including transducer, fixed reflector, and rotating reflector which effects scanning of the radial arc being tested by the sonic output from the transducer provides ultrasonic information which is processed through an ultrasonic signal processing system which digitizes, stores and displays the information.

1 Claim, 7 Drawing Sheets

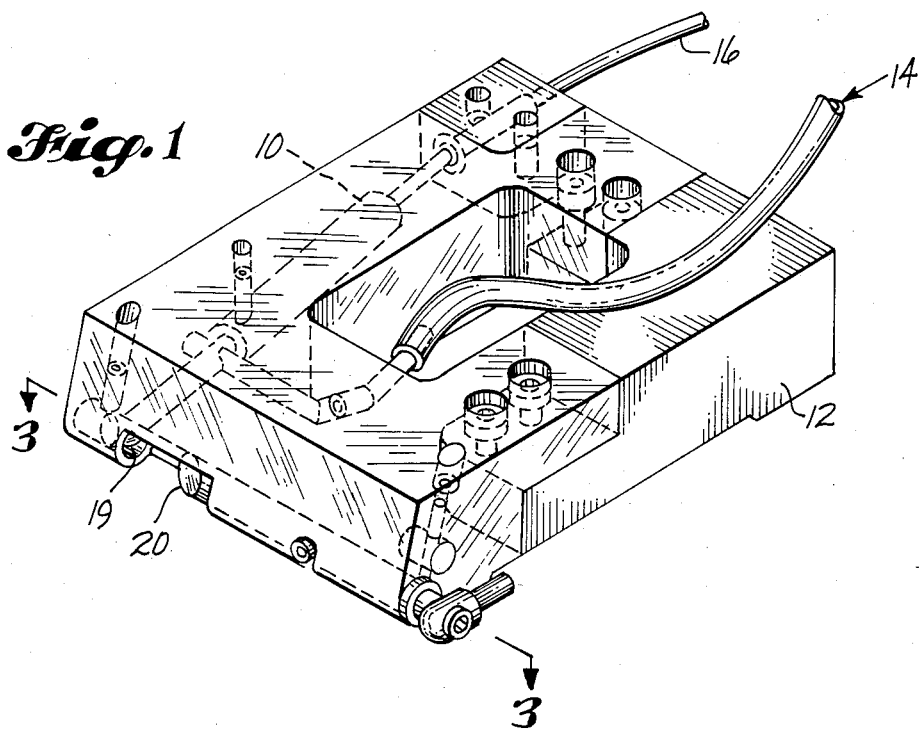
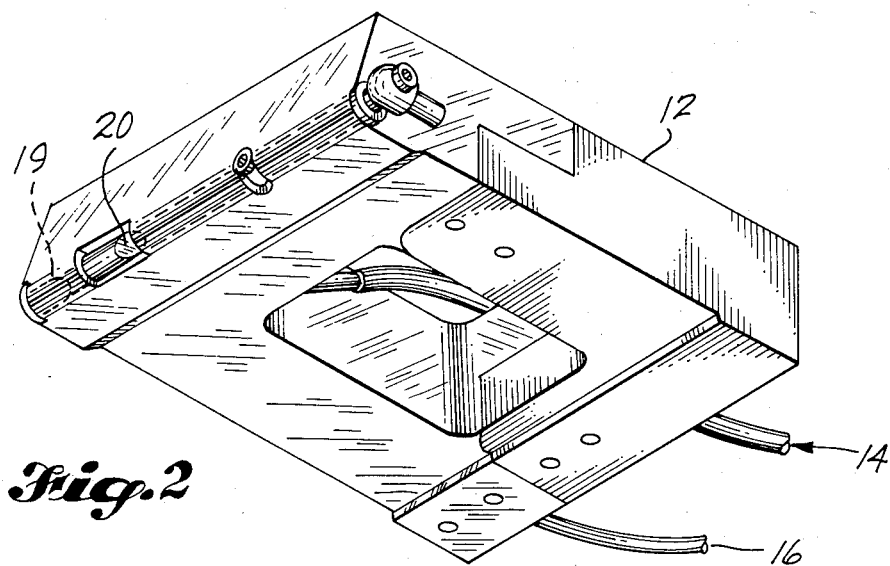

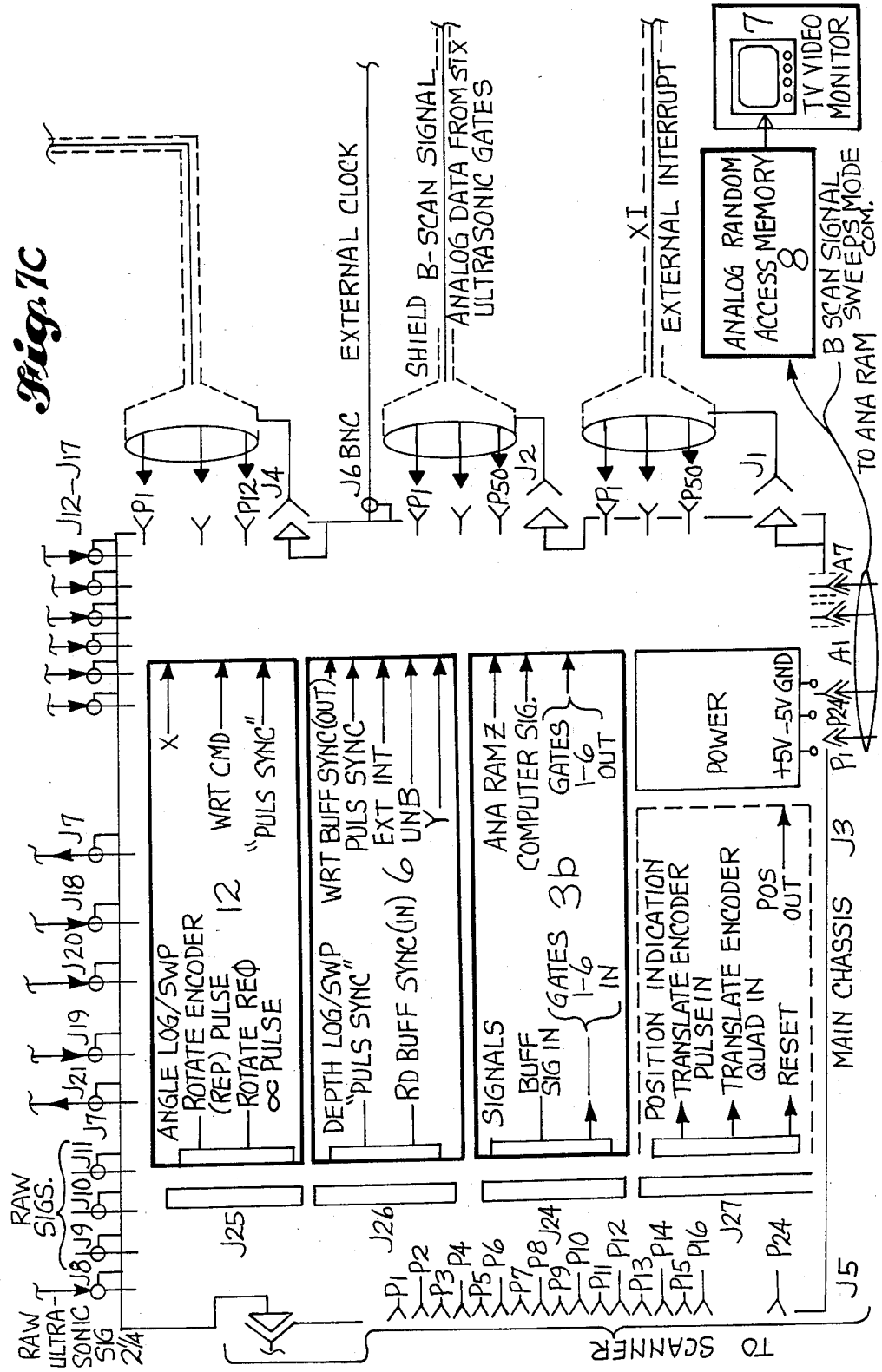

VARIABLE ANGLE TRANSDUCER SYSTEM AND APPARATUS FOR PULSE ECHO INSPECTION OF LAMINATED PARTS THROUGH A FULL RADIAL ARC

BACKGROUND OF THE INVENTION

This invention relates to ultrasonic scanning and detection systems and more particularly to ultrasonic scanning and detection systems capable of providing angular resolution through a full radial arc.

Prior art scanning arrangements have included systems as shown in U.S. Pat. Nos. 4,185,501 and 4,466,286. In contrast unique features of the present apparatus and system include a single transducer apparatus and detection system instead of an array of transducers, in which a full radial arc can be inspected in a single path.

Inside corners on metallic and non-metallic structural members frequently require inspection for delamination and cracks. The cross section of an inside corner is usually a circular arc of known radius. A complete examination of such areas requires the use of ultrasonic inspection. This inspection is difficult because the second beam must:

(a) physically scan across the radius to provide thorough coverage;
(b) remain perpendicular to the parts surface at all times to provide a known internal beam and a front surface echo for gaining setting and time reference; and
(c) be reliably coupled into the part.

Prior attempts have included the utilization of an ultrasonic shoe with a number of transducers oriented at different angles into the radius which systems however have not provided sufficient angular resolution nor provided a moving beam for display generation. In addition, in such systems portions of the radial arc remain uninspected because the transducer case and the part surface coincide at extreme angles. Use of a single transducer scanned by hand along the radial arc as done in the prior art does not provide reproducible data, and does not allow display generation, and does not inspect the extremes of the arc. Also, use of a single transducer mounted in a fixture and scanned along the radial arc does not inspect the extremes of the arc. Use of various through transmission methods provides no information on depth or angular position on the arc.

Use of methods which require that test parts be immersed in a tank of water to provide ultrasonic coupling is impractical. An oil covered, water filled boot mounted on the active face of the transducer provides unreliable coupling on rough surfaces.

It is accordingly an object of the present invention to provide a system and apparatus for pulse echo inspection of laminated parts through a full radial arc.

It is yet another object of the present invention to provide a system which includes motorized reflector control for producing an intensity modulated image in a television type video display. It is still another object of the present invention to provide a variable angle transducer positioner for radius inspection of graphite/epoxy blade stiffened structures to inspect a ninety degree window through a radius and delta areas. It is yet another object of the present invention to provide a variable angle transducer positioner utilizing a 2.25 (MHz) transducer coupled with two reflectors that project sound into a radius from its center point which ultrasonic transducer positioner enables variable angle ultrasonic inspection using the pulse-echo method with water as the couplet.

It is still another object of the present invention to provide a ultrasonic signal processing system for controlling mirror rotation in a variable angle transducer positioner apparatus thereby providing an interrogating sound beam which returns ultrasonic echoes in the presence of delaminations in a laminated part being inspected, the ultrasonic signal processing system further providing echo signal processing input signals to a video display device.

Further objects and advantages of the present invention will become apparent from the following detailed description hereinafter with reference to the accompanying drawings.

BRIEF DESCRIPTION OF THE DRAWINGS

FIG. 1 is a top perspective view of the present variable angle ultrasonic transducer positioner apparatus;

FIG. 2 is a bottom perspective view of the apparatus of FIG. 1;

DESCRIPTION OF THE PREFERRED EMBODIMENTS

Figure 4:
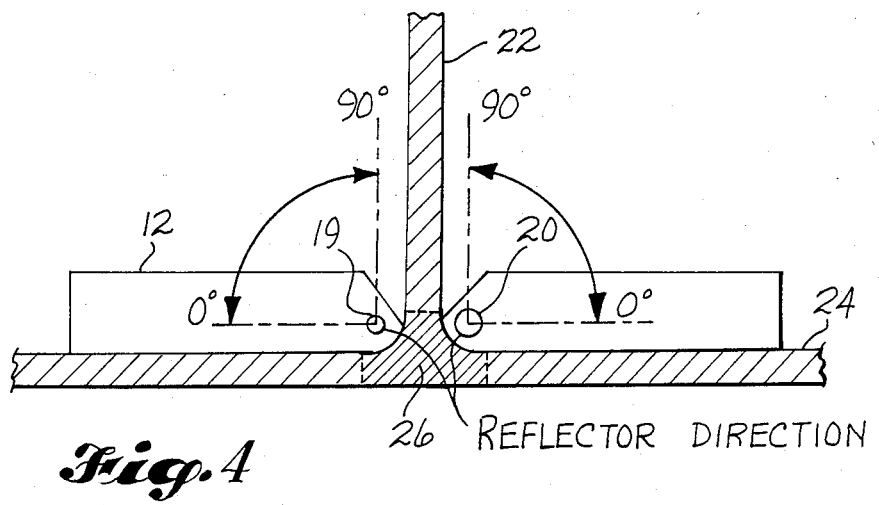
FIG. 4 is a diagrammatic view showing the method of inspection of the cross section of an inside corner which is usually a circular arc of known radius of a laminated structure when utilizing the variable angle ultrasonic transducer positioner apparatus of FIGS. 1 and 2.
Figure 3:
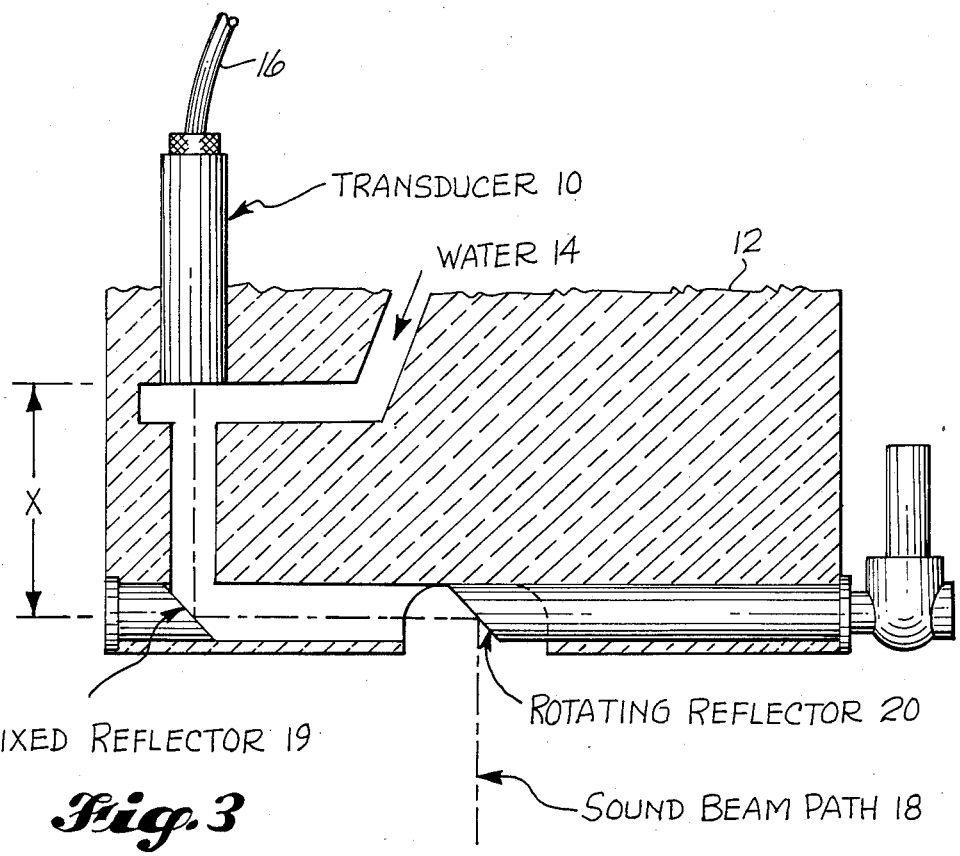
FIG. 3 is a cross section of the variable angle ultrasonic transducer positioner apparatus of FIG. 1 taken along the lines 3—3 helpful in understanding the method of operation thereof.

Turning now to FIGS. 1, 2, and 3 and the present variable angle ultrasonic transducer positioner apparatus which is suitable for hand-held positioning for pulse echo inspection of corners in laminated parts, it will be seen that a 2.25 (MHz) transducer 10 is mounted within a Lucite housing 12 and provides coupling of sound waves through water flow path 14 (as seen in FIG. 3) while transducer 10 is energized through transducer energization conductor 16 to which a suitable potential is applied. Sound beam path 18 (as seen in FIG. 3) utilizes a double reflector system. The present double reflector system is a 0.250 inch radius double reflector utilizing 2.250 inch stainless steel reflectors at a relative angle of ninety degrees with respect to each other; these angles being fixed, and not adjustable. The only adjustment possible is the movement of rotating reflector 20 for scanning in the actual inspection of a laminated part. Ninety degree rotation of rotating reflector 20 provides inspection through an angle of from zero degrees to ninety degrees. Angles utilized during actual inspection are zero degrees, forty-five degrees and ninety degrees which capability can be seen from FIG. 4. FIG. 4 shows the present variable angle ultrasonic transducer positioning apparatus housing 12 located at a typical inplace position. Stringer/blade 22 and skin 24 are shown, as is shadow inspection area 26. Sound beam path 18 emanating from transducer 10 as seen in FIG. 3 is first reflected ninety degrees by stainless steel fixed reflector 19 prior to reflection by stainless steel rotating reflector 20 for further transmission through the water flow path 14 into the inspection area 26 as seen in FIG. 4. Utilization of a prototype single-transducer positioner apparatus was attempted but failed since coaxial cable interference resulted and transducer diameters were too large and interfered with correct placement in the radius to be inspected. Such arrangement also was unable to accommodate the twenty to thirty degree blade angle layover. Parameters appeared to dictate that sound had to emanate from the center of the blade skin fillet radius which resulted in the present double reflector system shown in FIGS. 1-3. The variable angle ultrasonic transducer positioner apparatus of FIGS. 1-3 which use a double reflector system including a fixed reflector 19 and a rotating reflector 20 permits the generation of a sound beam which remains perpendicular to the parts surface at all times and which scans through 360° allowing inspection of the extremes of the radial arc. If the fixed reflector 19 is removed, the case of the transducer will coincide with the parts surface for small radii.

Coupling is obtained by filling the internal chamber 30 of housing 12 as seen in FIG. 3 with flowing water through a conduit 14 as seen in FIG. 1. The advantage of using the present ultrasonic rotating reflector 20 configuration are (1) a single transducer can be utilized instead of an array of transducers, (2) the full radial arc is inspected, and (3) a single path can be made to inspect the radius of the laminated part. In FIG. 3 the distance X is equal to the water travel distance required which is determined by a need to avoid 2nd water multiple.

Figure 5:
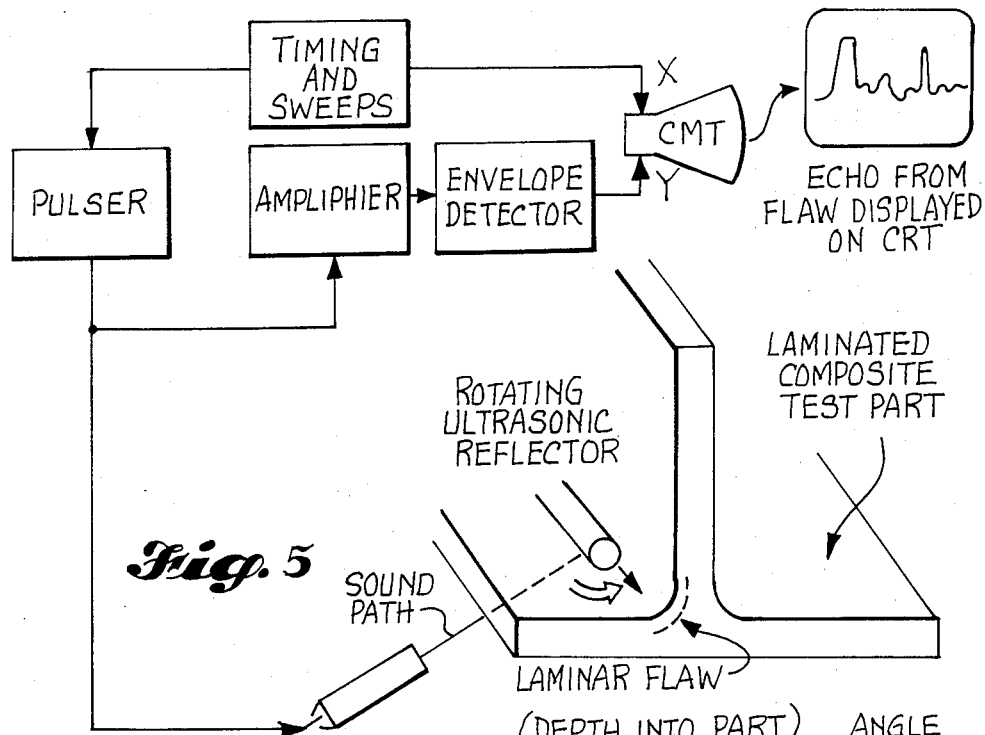
FIG. 5 is a schematic block diagram of the earlier first embodiment of the present ultrasonic signal processing system useful for processing signals from the variable angle transducer apparatus of FIGS. 1 and 2.

Turning now to FIG. 5, a block diagram of the preliminary design first embodiment is seen wherein the transducer signal processing path at lead 16 is seen coupled to the ultrasonic signal processing system which provide it an echo from flaw which was displayed on a CRT. Actual labels on the blocks of the block diagram describe the standard components used for signal processing to provide the display on the CRT. This first embodiment block diagram is included to show the differences between the first embodiment and the improved working embodiment shown in FIG. 6 and shows ultrasonic signal processing system 100 coupled downstream from ultrasonic transducer 10 through transducer connector cable 16. The variable angle transducer positioner apparatus of the system of FIG. 5 provided ultrasonic pulse echo inspection of corners in laminated parts. For such parts the inspected flaws are delaminations which occur in planes parallel to the surface of the part. The ultrasonic apparatus with rotating reflector 20 injected sound into the laminated composite test part 24 perpendicular to the surface throughout the entire angular sweep of the radius or corner. This is the proper sound direction for the detection of the aforementioned delaminations. The operator used one hand to move the scanner to a suspect location and the other hand to rotate the mirror in the first prototype thereby scanning the sound through the curved corner. Downstream signal processing provided an ultrasonic pulser/receiver and display was utilized to examine echoes produced by flaws.

Figure 6:
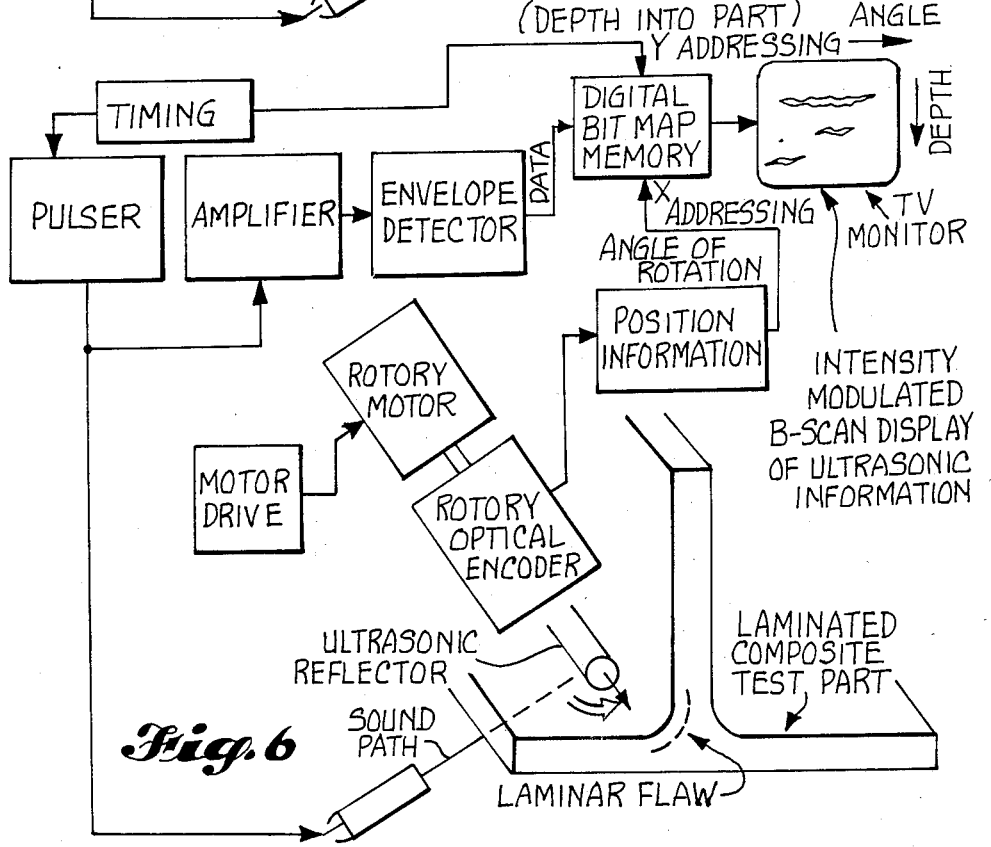
FIG. 6 is a later second embodiment of the present ultrasonic signal processing system shown in schematic block diagram; and, FIGS. 7A through D is a complete schematic block diagram showing in detail the second embodiment system of FIG. 6.
Figure 7A:
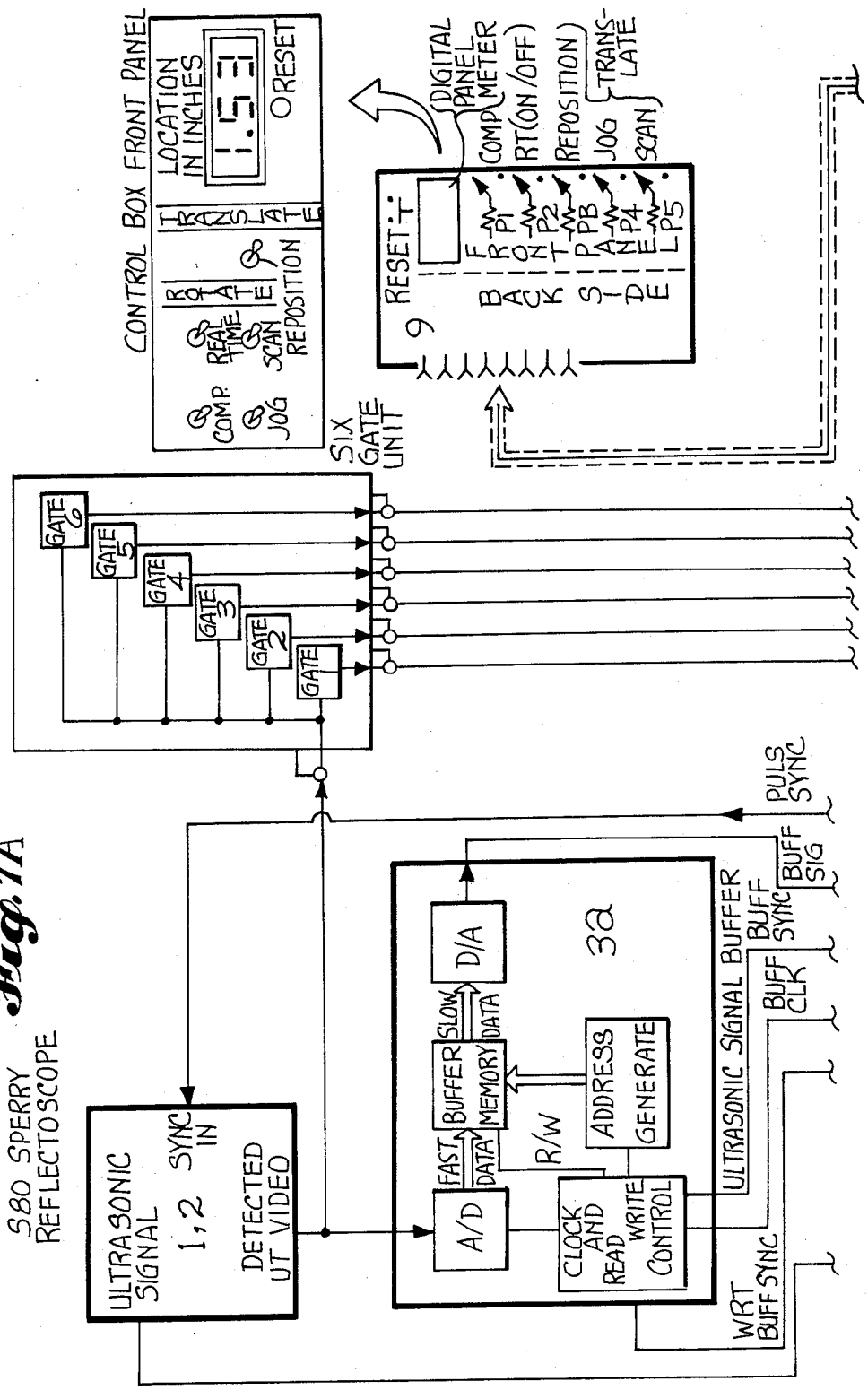
Figure 7B:
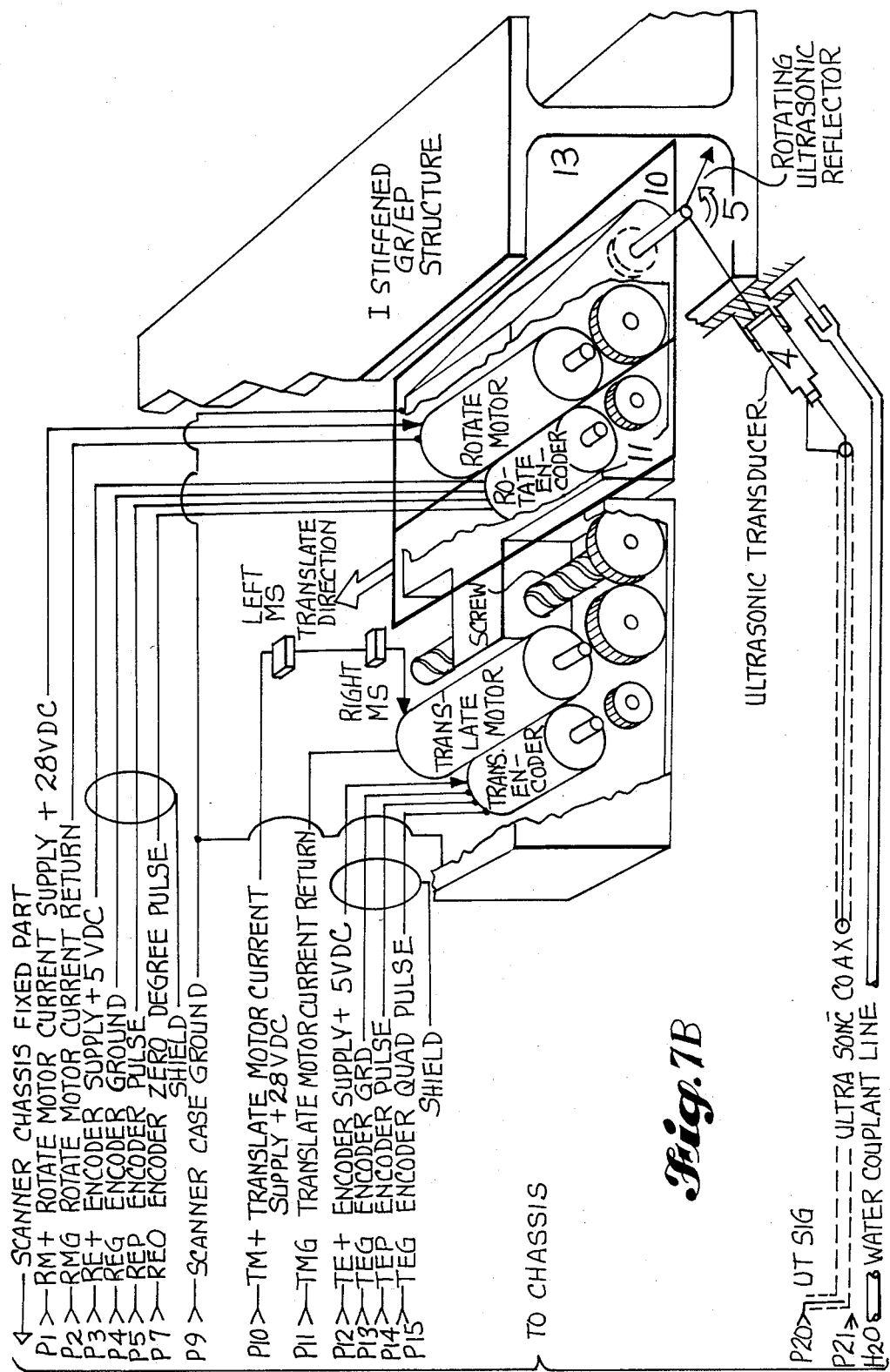
Figure 7D:
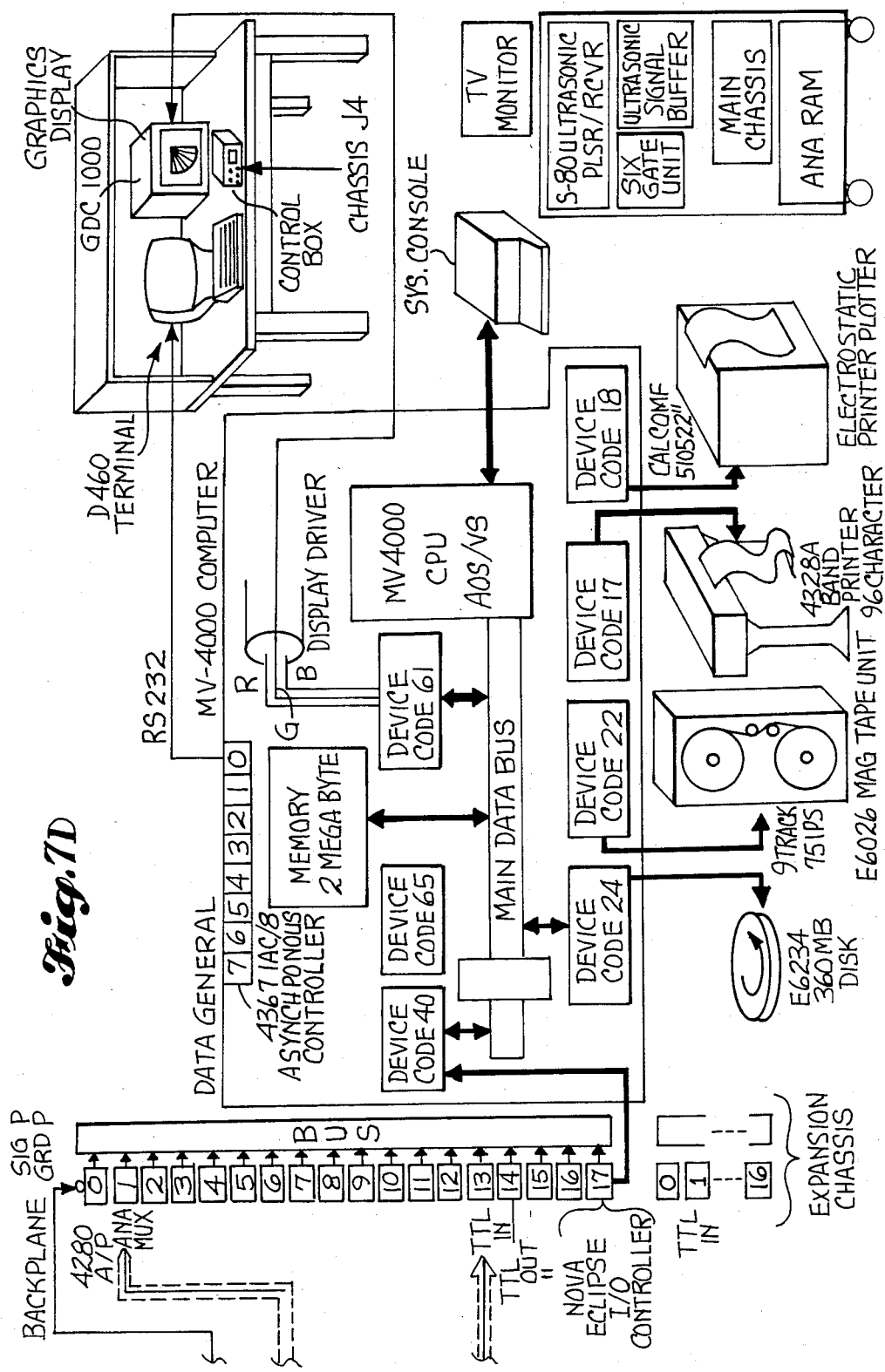

In the present embodiment of FIG. 6 mirror rotation was motorized to increase the data rate an estimated fifty times. It would have been impossible to interpret data at that rate looking at a conventional CRT display as utilized in the early prototype first embodiment of FIG. 5. Therefore a real time B-scan display was utilized in the system of FIG. 6. With such display and the ultrasonic signal processing system of FIG. 6 the inspector could observe in the TV monitor 7 of FIG. 6 the incoming data and interpret all of the incoming data.

The description herein now is made with reference to the block schematic diagram of FIG. 6, and FIGS. 7A-D may be referred to for a detailed electrical schematic diagram of the system of FIG. 6. It should be noted that all of the key elements of the system of block diagram 6 have been superimposed on the full schematic diagram of FIGS. 7A-D so that quick reference and understanding of the full schematic operation of FIGS. 7A-D can be easily understood.

Turning now to the block diagram of the second embodiment of the present ultrasonic signal processing system it should be noted that an on/off switch in motor drive and control circuit 9 causes rotation of the motor 10. Motor rotating circuits 10 drive both optical encoder circuit 11 and ultrasonic mirror 5.

Pulses from optical encoder 11 are accumulated in position information circuits 12 thereby providing mirror angular position information. This information provides bit map row address values for digital bit map memory circuit 8.

Pulses from rotary optical encoder circuit 11 also cause activation of ultrasonic pulser/receiver circuits 1. Pulses from ultrasonic pulser receiver circuit 1 activate the sound source 4 provided by ultrasonic transducer 10. Sound from ultrasonic transducer 4 is reflected by rotating mirror 5 so that the beam is caused to rotate through the corner of the laminated composite test part 24, the beam remaining perpendicular to the curved corner surface at all times. Laminated test part 13 is thereby exposed to an interrogating sound beam which returns ultrasonic echoes in the presence of rejectable delaminations. Sound source 4 provided by transducer 10 receives these echoes and converts them into electronic signal information. Amplifier detector circuits 2 amplifies these signals downstream and removes the oscillations from the waveform of the signal transmitted thereby producing an envelope detected signal. Envelope buffer circuit 3 performs analog to digital conversion and presents the signals as data values to digital bit map memory circuit 8 downstream.

Pulses from rotary optical encoder circuit 11 also activate timing circuit 6 which provides bit map column address information to digital bit map memory 8. Data is read from digital bit map memory 8 in a television type video format and presented to TV monitor output display device 7. The inspector operator of the present variable angle transducer system and apparatus manually moves the present variable angle ultrasonic transducer positioner apparatus along the part while viewing the image on the TV monitor. Abnormal deviations from the standard pattern for a good part are interpreted as flaws thereby providing for accurate inspection of the part.

We claim:
1. An ultrasonic variable angle scanning apparatus comprising in combination:
a housing;
a fixed reflector mounted in said housing for reflecting incident sound wave energy ninety degrees;
a rotating reflector axially disposed with respect to said fixed reflector, said rotating reflector providing rotation of sound wave energy received from said fixed reflector about a radial arc which cuts through the part under inspection.

* * * * *